United States Patent [19]

Hanig

[11] Patent Number: 5,080,645
[45] Date of Patent: Jan. 14, 1992

[54] PROCEDURE FOR REDUCING THE BODY BURDEN OF HIV (AIDS) AND OTHER BLOOD BORNE INFECTIONS

[76] Inventor: Joseph P. Hanig, 822 Eden Ct., Alexandria, Va. 22308

[21] Appl. No.: 429,623

[22] Filed: Oct. 31, 1989

[51] Int. Cl.$^5$ .................... A61M 3/00; A61N 5/00
[52] U.S. Cl. .................................. 604/4; 604/49; 604/52; 128/898; 514/832
[58] Field of Search ............... 604/4, 49, 52, 7, 51, 604/48, 5; 128/898, 897; 514/661, 832

[56] References Cited

U.S. PATENT DOCUMENTS

| | | | |
|---|---|---|---|
| 4,520,109 | 5/1985 | Simmonds et al. | 436/56 |
| 4,737,140 | 4/1988 | Lee et al. | 604/4 |
| 4,772,840 | 2/1988 | Valenzuelal et al. | 424/88 |
| 4,787,883 | 11/1988 | Froyer | 604/4 |
| 4,824,432 | 4/1989 | Skurkovich et al. | 604/4 |
| 4,833,165 | 5/1989 | Louderback | 514/694 |
| 4,846,789 | 12/1989 | Heitz et al. | 604/49 |
| 4,865,841 | 9/1989 | Balint et al. | 424/85.8 |
| 4,878,891 | 11/1989 | Judy et al. | 604/5 |
| 4,923,442 | 5/1990 | Segall et al. | 604/52 |
| 4,931,472 | 6/1990 | Erner | 514/661 |

OTHER PUBLICATIONS

Current Surgery, vol. 45, 1988, pp. 365-370; Blood Substitutes: Where Do We Stand With The Fluorocarbon Approach?; Jean G. Riess, Ph.D.
Biomat., Art. Cells, Art. Org., 16(1-3), 31-49 (1988); Perfluorochemicals As Oxygen Transport Vehicles; Robert P. Geyer, Ph.D.
Cecil Textbook of Medicine, 18th Edition, Common Poisonings; pp. 143-145, W. R. Sanders Co., Philadelphia (1988).
Gilman & Goodman, The Pharmacological Basis of Therapeutics, 7th Edition, Chapter 70, Pesticides, p. 1641, McMillan Publishing Co., N.Y. (1985).
Abstract of: Am. J. Obstet. Gynecol. 1984 Apr. 1; 148(7):859-67; Maternal And Fetal Effects Of Exchange Transfusion With A Red Blood Cell Substitute; R. C. Cefalo et al.
Abstract of: Arch. Pathol. Lab. Med. 1985 Apr.; 109(4):340-4; Some Long-Term Effects Of Exchange Transfusion With Fluorocarbon Emulsions In Macaque Monkeys; W. I. Rosenblum et al.
Abstract of: J. Clin. Pathol. 1987 May; 40(5)505-7; Painful Sickle Cell Crises Precipitated By Stopping Prophylactic Exchange Tranfusions; A. J. Keidan.
Abstract of: J. Toxicol. Clin. Toxicol. 1988; 26(5-6):3-57-64; Treatment Of Aniline Poisoning With Exchange Transfusion; R. J. Mier.
Abstract of: Clin. Pediatr. (Phila) 1982 Oct.; 21(10):602-6; Efficacy Of Phototherapy And/Or Exchange Transfusions In Neonatal Jaundice; N. Kalpoyiannis et al.
Abstract of: Clin. Pediatr. (Phila) 1989 Oct.; 28(10):480-1; Recovery From Respiratory Paralysis Caused By Guilain-Barre Syndrome In An Infant After Repeated Exchange Transfusions; S. Singh et al.
Abstract of: Br. Med. J. (Clin. Res.) 1985 Oct. 26; 291(6503):1169-70; Exchange Transfusion And Quinine Concentrations In Falciparum Malaria; A. Hall et al.
Abstract of: JAMA; 1983 Jan. 14; 249(2):244-5; Fulminant Plasmodium Falciparum Infection Treated With Exchange Blood Transfusion; S. L. Kramer et al.
Abstract of: Am. J. Obstet. Gynecol. 1989 Fed; 160(2):407-11; Intravascular Exchange And Bolus Transfusion In The Severely Isoimmunized Fetus; S. Ronkin et al.
Abstract of: Am. J. Dis. Child. 1982 Jul.; 136(7):643-4; Extreme Leukocytosis Successfully Managed By Double-Volume Exchange Transfusion In An Infant With T-Cell Leukemia; J. D. Dickerman.
Abstract of: Pediatrics 1984 Nov.; 74(5):800-3; Changes In Auditory Brainstem Responses In Hyperbilirubinemic Infants Before And After Exchange Transfusion; C. G. Nwaesei et al.
Abstract of: Arch. Dis. Child 1983 Aug.; 58(8):631-3; Neonatal Paracetamol Poisoning: Treatment By Exchange Transfusion; S. Lederman et al.
Casarett & Doull, Toxicology—The Basic Science, 3rd Edition; Clinical Toxicology; p. 889.
Casarett & Doull, Toxicology—The Basic Science, 3rd Edition; Toxic Agents; pp. 586-588.
Casarett & Doull, Toxicology—The Basic Science, 3rd Edition; Applications Of Toxicology; pp. 880-881.
Casarett & Doull, Toxicology—The Basic Science, 3rd Edition; Toxic Effects Of Pesticides; pp. 551-552.
Cecil Textbook of Medicine, 18th Edition, pp. 1052-1053, W. B. Sanders Co., Philadelphia (1988).

Primary Examiner—C. Fred Rosenbaum
Assistant Examiner—Mark O. Polutta
Attorney, Agent, or Firm—Foley & Lardner

[57] ABSTRACT

The foregoing emergency replacement procedure or method for rapid and drastic reduction of the body burden of AIDS virus residing primarily in the formed elements of the blood involves the removal of all blood from the patient and replacement with an emulsion of a perfluorocarbon chemical or other blood substitute, several exchanges of blood substitute in order to attempt a "scrubbing" in totality of the AIDS containing blood from all of the tissues and organs served by vascular beds and then replacement of the emulsion of perfluorocarbon chemical or other blood substitute with whole blood of the same type as the patient; and wherein the above replacement procedure is carried out using antiviral agents or other agents currently shown to reduce, mitigate or destroy the AIDS virus during and after the above said replacement procedure.

27 Claims, No Drawings

PROCEDURE FOR REDUCING THE BODY BURDEN OF HIV (AIDS) AND OTHER BLOOD BORNE INFECTIONS

BACKGROUND OF THE INVENTION

AIDS disease first detected in significant numbers of patients in 1981, named in 1982 and characterized in 1983 in France and in 1984 in the U.S. is a virus that invades the genetic material of immunologically competent cells destroying them and ultimately killing 100% of all victims who die of opportunistic diseases such as Kaposi's sarcoma and pneumocystis carinii pneumonia. The virus is thought to reside largely within the helper T cell of the blood and to compel rapid multiplication of the virus by the genetic apparatus of this and similar immunocompetent cells which ultimately die and release more HIV virus to invade other cells. The incubation time is now thought to be 5 to 7 years with the manifestation of the disease initially signalled by the appearance of AIDS positive antibodies. This is generally followed by various signs of malaise including weakness, reduction of appetite, severe weight loss and increasing susceptibility to infections and viral invasions that are normally prevented or defeated by the competent immune system of the uninfected healthy individual. Death usually ensues within eighteen months to several years after the appearance of symptoms, although there have been some notable exceptions, and current drug therapy appears to be extending survival time to a limited extent.

The approach to therapy has gone in several directions. Naturally, the initial thrust was directed towards the symptomatic treatment of the opportunistic diseases that were the cause of death at the terminal stages. These attempts included the use of anticancer drugs for the Kaposi's sarcoma and a variety of antibiotic or antiviral drugs for the pneumocystis carinii. A more recent approach has included the development of several drugs designed to block the replication of the virus in the interior of the cell and AZT and DDI are two of the more successful of these attempts. AZT is now being used extensively. It is very expensive, quite toxic to bone marrow (and because of this may not be used in all patients) and seems only to retard the progression of the disease by slowing the multiplication of the HIV virus, but it does not reverse the process. DDI seems to show much greater promise and early reports include evidence of reduction of viral titers as well as weight gain and reappearance of vitality in some patients.

Another approach to therapy has involved the attempt to develop a vaccine for the virus. Early efforts based on a variety of approaches involving the use of a portion of the outer protein coat as an antigen to produce antibodies have been unsuccessful because the complexity of the glycoprotein does not encourage extensive antibody production. Also, since the AIDS virus resides within the interior of the cell access is limited in infected cells and in other cases the virus appears to be capable of mutation that allows avoidance or escape from the antibody that would destroy it. Currently a number of other approaches are being attempted that incorporate a variety of recombinant techniques. These involve replication of portions of viral proteins that might be used to stimulate the immune system, inserting the gene for one of the AIDS antigen glycoproteins into vaccinia virus, the use of anti-idiotypes to stimulate the immune system in an identical way as the AIDS virus without the immune cell toxicity and creation of copies of the helper T cell receptor that AIDS virus attaches to as a strategy to tie up and titrate the virus before it attaches to susceptible cells. Finally, there are the older more traditional approaches that utilizes whole killed AIDS virus to stimulate the immune system.

In general, all of these approaches involve one of three regimes: blockade of replication of the AIDS virus, or its immunological destruction by antibodies, or its sequestration by receptor duplicates and perhaps eventually blockade of attachment to actual T cell receptors. All of these approaches however, do not address what could be an immediate approach to reduction of the body burden of the virus regardless of the phase of infection or the stage of progression of the disease. In fact, the failure of several therapeutic approaches when tried in patients, even though they showed so much promise in vitro, have been attributed to the overwhelming amount of virus that exists in infected humans or the animal model in comparison to the amount present in tissue culture testing. There is very little doubt that the effectiveness of any of the above approaches, particularly the use of antivirals to block replication of the virus, would be enhanced and the probability of success heightened if the amount of virus in the body could be drastically diminished.

In fact, a recent report in SCIENCE (July 21, 1989) has demonstrated that the body burden of AIDS virus is far greater than suspected earlier, namely that at least one in one hundred white blood cells (CD4 positive T4 cells) are infected rather than one in ten thousand, an increase of one hundred fold. This appears to be an extremely high number of infected cells as stated by the authors who performed the work. This publication also indicates that there is ten times higher level of rapidly replicating AIDS virus in patients then was previously thought.

SUMMARY OF THE INVENTION

The foregoing emergency replacement procedure or method for rapid and drastic reduction of the body burden of AIDS virus residing primarily in the formed elements of the blood involves the removal (to the extent that it is clinically possible) of all blood from the patient and replacement with an emulsion of a perfluorocarbon chemical or other blood substitute (in physiological saline or equivalent isoosmotic) in order to attempt a "scrubbing" in totality of the AIDS containing blood from all of the vital organs and then replacement of the emulsion of perfluorocarbon chemical or other blood substitute with whole blood of the same type as the patient. Originally, Geyer (New England J. of Medicine, vol. 289, no. 20, Nov. 15, 1973, p.1080) demonstrated that rats totally perfused with a fluorocarbon emulsion (so called "bloodless rats") survived up to nine months which was the time of publication of this article, whereas those rats undergoing 90-97% replacement of blood had already survived over two years and lived essentially normal lives. It has been established in humans by Mitsuno et al (Ann. Surg. vol. 95, no.1, Jan. 1982) that the emulsion Fluosol-DA (20%) is a useful substitute as an artificial oxygen transport medium used in emergency surgery when massive amounts of fluid must be transfused to replenish intravascular volume. It has been shown in various animal models (e.g. Engelman et al in the Ann. Thor. Surg. vol.

32, no. 6 Dec. 1981) that nearly all the blood can be replaced and the blood substitute can sustain life for many hours, if not days. It is thought that the above stated replacement procedure would add months, perhaps, years to an AIDS infected patient's life span particularly if antiviral agents such as AZT or DDI or other similar agents are introduced at their currently used concentrations with the number of target white bloods cells drastically reduced, thus enhancing drug to virus ratio. It is also thought that this procedure would be better than using whole blood because in a total replacement procedure the interface between the newly formed blood elements, the patient's old blood and the newly introduced blood is not well defined and there would be diffusion and mixing of the new and old formed blood elements and a significant amount of the contaminated blood would remain.

DESCRIPTION OF THE PREFERRED EMBODIMENTS

In a patient infected with AIDS or a similar virus the following replacement procedure for rapidly and dramatically reducing the body burden of these viruses such as AIDS by completely removing, as is clinically possible, all blood from the patient and replacing it with an emulsion (in physiological saline or equivalent isosmotic solution having the proper viscosity) of perfluorocarbon compounds or other synthetic blood substitutes that are capable of sustaining life by picking up and releasing oxygen with similar effectiveness as hemoglobin. Conducting said replacement procedure under clinical cryogenic conditions of lowered body temperature in order to reduce the body's need for oxygen, or alternatively supplying the patient with supplementary oxygen up to 100% under the conditions of ambient temperature, or the use of hyperbaric conditions.

Performing several total exchanges of the emulsion of the perfluorocarbon compounds or other blood substitutes in order to attempt a "scrubbing" in totality of the virus contaminated blood from all of the vital organs as well as all other areas served by the vascular beds in the body.

By way of example, but not in any way a limitation, perfluorocompounds can include: Fluosol-DA 20% (emulsion of perfluorodecalin and perflurotripropylamine, available from Alpha Therapeutic Corporation, Los Angeles CA, as manufactured by Green Cross Corporation, Osaka, Japan); Fluosol-DC (FDC-perfluorodecalin, PPS Green Cross); FC-47 perfluorotripropylamine; FC-43; F-dimethyl-adamantine and F-trimethylbicyclononane (Suntech, Marcus Hook, PA). By way of further example, but again not of any limitation, other blood substitutes which can be used in accordance with this invention include hemoglobin and cross-linked hemoglobin substitutes, including pure polymerized bovine hemoglobin (Biopure Corporation, Boston, Mass. See Vlahakes et al., *J. Thorac. Cardiovasc. Surg.*, Vol. 100, 379-88 (1990)), and microencapsulated hemoglobin.

Replacing the emulsion of perfluorocarbon compounds or other blood substitute with whole blood of the same type as the patient (or typed red blood cells in a physiological solution followed by typed whole blood, whichever is more clinically appropriate) in a manner that sustains life and avoids cardiovascular collapse or emboli that would produce death.

Optionally using antiviral agents or other agents shown to reduce, mitigate or destroy AIDS virus in the above stated emulsion or blood substitute or applying said antiviral agents after the above stated replacement procedure or a combination of using antiviral agents in the emulsion and continuing the use after the emulsion is replaced by typed whole blood.

Optionally using a blood substitute that is the patient's own blood that has been cell sorted so as to contain only red blood cells in plasma or physiological solution; or the said blood substitute is typed red cells in plasma or physiological solution.

Optionally the replacement procedure involves a partial replacement using a combination of whole blood with perfluorocarbon emulsion or other blood substitutes or fresh whole blood of the patient's type to effect a partial reduction of the body burden of the AIDS or AIDS-like virus or other blood-born infections.

In general it is contemplated that the above replacement procedure would be effective in reducing the body burden of any toxicant, contaminant or product of disease (leukemia, blood poisoning infection, abberant enzyme etc.) that is primarily blood born and exerts its major toxicity from that compartment of the body.

While preferred embodiments of the present invention have been described, it will be understood that changes and modifications can be made therein without departing from the invention in its broader aspects. Various features of the invention are defined in the following claims.

I claim:

1. A method for reducing the body burden of a blood borne infection in a patient comprising the steps of:
    A) substantially or completely replacing the blood of a patient having a blood born infection with a synthetic blood substitute, and as part of a continuous process;
    B) subsequently replacing said synthetic blood substitute with whole blood, thereby reducing the number of infected cells in said patient.

2. The method of claim 1, wherein after step A but before step B, said synthetic blood substitute is partially or substantially completely replaced one or more times with additional quantities of a synthetic blood substitute.

3. The method of claim 1, wherein steps A and B are carried out under clinical cryogenic conditions of lowered body temperature which reduce the patient's need for oxygen.

4. The method of claim 1, wherein steps A and B are carried out under conditions of supplemented oxygen up to 100%.

5. The method of claim 1, wherein steps A and B are carried out under conditions of hyperbaric pressure.

6. The method of claim 1, wherein steps A and B are carried out as rapidly as clinically possible.

7. The method of claim 1, wherein at least one therapeutic agent for said blood born infection is administered to said patient in said synthetic blood substitute, concurrently with said synthetic blood substitute, or subsequent to step B.

8. The method of claim 1, wherein said synthetic blood substitute comprises a perfluorocarbon compound.

9. The method of claim 1, wherein said synthetic blood substitute comprises a synthetic hemoglobin substitute.

10. A method for reducing the body burden of AIDS virus in a patient having AIDS comprising the steps of:
   A) substantially or completely replacing the blood of an AIDS patient with a synthetic blood substitute, and as part of a continuous process;
   B) replacing said synthetic blood substitute with whole blood, thereby reducing the number of infected cells in said patient.

11. The method of claim 10, wherein after step A but before step B, said synthetic blood substitute is partially or substantially completely replaced one or more times with additional quantities of a synthetic blood substitute.

12. The method of claim 10, wherein steps A and B are carried out under clinical cryogenic conditions of lowered body temperature which reduce the patient's need for oxygen.

13. The method of claim 10, wherein steps A and B are carried out under conditions of supplemented oxygen up to 100%.

14. The method of claim 10, wherein steps A and B are carried out under conditions of hyperbaric pressure.

15. The method of claim 10, wherein steps A and B are carried out as rapidly as clinically possible.

16. The method of claim 10, wherein at least one therapeutic agent for said AIDS infection is administered to said patient in said synthetic blood substitute, concurrently with said synthetic blood substitute, or subsequent to step B.

17. The method according to claim 10, wherein said synthetic blood substitute comprises a perfluorocarbon compound.

18. The method according to claim 11, wherein said synthetic blood substitute comprises a perfluorocarbon compound.

19. The method according to claim 12, wherein said synthetic blood substitute comprises a perfluorocarbon compound.

20. The method according to claim 13, wherein said synthetic blood substitute comprises a perfluorocarbon compound.

21. The method according to claim 14, wherein said synthetic blood substitute comprises a perfluorocarbon compound.

22. The method according to claim 15, wherein said synthetic blood substitute comprises a perfluorocarbon compound.

23. The method according to claim 16, wherein said synthetic blood substitute comprises a perfluorocarbon compound.

24. The method of claim 10, wherein said synthetic blood substitute comprises a synthetic hemoglobin substitute.

25. The method of claim 11, wherein said synthetic blood substitute comprises a synthetic hemoglobin substitute.

26. The method of claim 12, wherein said synthetic blood substitute comprises a synthetic hemoglobin substitute.

27. The method of claim 13, wherein said synthetic blood substitute comprises a synthetic hemoglobin substitute.

* * * * *